United States Patent [19]

Rohwer

[11] Patent Number: 4,784,851

[45] Date of Patent: Nov. 15, 1988

[54] COMPOSITION FOR TREATMENT OF ACIDOSIS IN RUMINANTS AND METHOD

[76] Inventor: Gary L. Rohwer, Sharp Ln., Parma, Id. 83660

[21] Appl. No.: 27,070

[22] Filed: Mar. 17, 1987

Related U.S. Application Data

[63] Continuation of Ser. No. 712,505, Mar. 18, 1985, abandoned.

[51] Int. Cl.$^4$ .................. A61K 31/10; A61K 33/00
[52] U.S. Cl. .................. 424/156; 424/127; 424/438
[58] Field of Search .................. 424/438, 127, 156

[56] References Cited

U.S. PATENT DOCUMENTS

| | | | |
|---|---|---|---|
| 139,954 | 6/1883 | Hall | 424/156 |
| 1,467,455 | 9/1923 | Schmid | 424/127 |
| 1,618,051 | 11/1924 | Bradley | 424/125 |
| 3,538,214 | 11/1970 | Polli | 424/19 |
| 4,005,191 | 1/1977 | Clark | 424/154 |
| 4,289,750 | 9/1981 | Kopp et al. | 424/154 |
| 4,303,648 | 12/1981 | Witzel et al. | 424/156 |
| 4,405,596 | 9/1983 | Helbig et al. | 424/154 |

FOREIGN PATENT DOCUMENTS

| | | | |
|---|---|---|---|
| 1036941 | 8/1978 | Canada | 424/156 |
| 2541337 | 3/1977 | Fed. Rep. of Germany | 424/127 |
| 0037827 | 3/1979 | Japan | 424/127 |

OTHER PUBLICATIONS

Blodinger—*Formulation of Veterinary Dosage Forms,* Marcel Decker, Inc., N.Y., pp. 157–160.
*Chemical Abstracts,* vol. 74 (1971), 2604b; vol. 77 (1972), 73262; vol. 77 (1972), 70330w; vol. 91 (1979), 18140d.
Blood et al., Veterinary Medicine, 3rd Edition, date unknown, pp. 157–158.
Dunn et al., Journal of Animal Science 48, No. 4, 764–769 (1979).
The Merck Veterinary Manual, 4th Ed., 140–141 (1973).
Prescriptions, p. 1526, RX 469, date unknown.
*Chemical Abstracts,* vol. 56, (1962) 12249b; vol. 59 (1963) 4418d; vol. 64 (1966) 18281g.
*Chemical Abstracts,* vol. 66 (1967), 9825d.

*Primary Examiner*—Frederick E. Waddell

[57] ABSTRACT

A paste-consistency composition consisting essentially by weight of from about 40% to about 60% of a source of alkalinity selected from the group consisting of nontoxic carbonates, bicarbonates and sesquicarbonates, from about 15% to about 40% fatty vehicle and from about 5% to about 40% thickener is applied to the tongue of a ruminant for treatment of acidosis.

9 Claims, No Drawings

COMPOSITION FOR TREATMENT OF ACIDOSIS IN RUMINANTS AND METHOD

This application is a continuation of application Ser. No. 712,505, filed Mar. 18, 1985, now abandoned.

TECHNICAL FIELD

This invention relates to the treatment of ruminants for acidosis.

The term "ruminant" is used herein in a broad sense as including animals that chew the cud and have a plurality of stomach chambers including a first chamber referred to as a rumen. Ruminants include, for example, cattle (both beef and milk cattle, e.g. bulls, steers and cows), sheep, buffalo, goats, camels, reindeer, water buffalo, elk, deer and giraffes. As used herein, the term "acidosis" means an excess of lactic acid in the rumen and the harmful results that are caused by this.

BACKGROUND OF THE INVENTION

Acidosis in ruminants is normally caused by a feed overload. This occurs, for example, because of a feed error (e.g. too much grain because of accidentally feeding a finish ration instead of a normal ration) or because of a feed breakdown (e.g. because the weather or other cause prevents the animals from eating) followed by overeating. When the feed overload occurs, the bacteria in the rumen have not had a chance to adapt to the temporary situation and produce an excess of lactic acid. The harmful results that occur include the death of rumen bacteria and passage of lactic acid through the rumen wall into the bloodstream to lower the systemic pH. The death of rumen bacteria results in interference with the animal's digestion. The lowering of systemic pH can inhibit nervous system function and muscle response and can result in death.

According to the Merck Veterinary Manual (4th edition), one preferred treatment of acidosis involves emptying the rumen contents and replacing such with rumen contents from a healthy animal, and an alternative treatment involves emptying the rumen contents, irrigating the rumen 15 to 20 times and using balanced electrolytes to correct acid-base imbalance and dehydration and to restore renal function. These treatments are impractical especially if a plurality of animals are affected. Other treatments disclosed in Merck consist of oral drenching with calcium carbonate or magnesium hydroxide solutions. These treatments are not very effective and can lead to bloat.

Sodium bicarbonate has been used in the treatment of rumen acidosis. However, such use presents difficulties. For example, if an aqueous solution of sodium bicarbonate is pumped into an acidotic animal's rumen, large quantities of carbon dioxide quickly form and the animal has difficulty eructating these because of reduced muscle response; this leads to bloat and the risk of pressure on the animal's heart and death.

Dunn, B. H., Emerick, R. J. and Embry, L. B., Journal of Animal Science 48, No. 4 (1979) report some success in preventing acidosis in feed overload situations by including in the feed sodium bentonite and/or sodium bicarbonate. This is not a satisfactory solution because continued feeding does not result in continued weight gain improvement and because a higher incidence of urinary calculi was noted in lambs and steers on a continuing diet (maintenance doses) including sodium bicarbonate.

SUMMARY OF THE INVENTION

It has been discovered herein that the disadvantages of maintenance doses of sodium bicarbonate in feed are overcome and that bicarbonate as well as carbonate and sesquicarbonate can be used to treat acidosis in ruminants if lactic acid in the rumen is gradually neutralized by controlled release of the bicarbonate or other source of alkalinity from a paste formulation. The slow release offers protection against the harmful effects of bloat.

A first mechanism involves controlled release of the treatment composition into the rumen. This is accomplished by using treatment composition in the form of a paste having a consistency similar to peanut butter and applying it to the animal's tongue whereby the composition cannot be spit out or swallowed all at once and is instead gradually swallowed, for example, over a period ranging from about two to 10 minutes. Moreover, the consistency is such that it promotes a tendency for the animal to roll its tongue thereby obtaining the same motion as is required to eruct controllably generated gas.

A second mechanism involves using the source of alkalinity in combination with a fatty vehicle which interferes with immediate contact and reaction of all of the source of alkalinity with the excess lactic acid and thus provides controlled release of alkaline neutralizing agent in the rumen.

The composition of the present invention for treating acidosis in ruminants consists essentially by weight of (a) from about 40% to about 60% of a source of alkalinity selected from the group consisting of non-toxic carbonate, bicarbonate and sesquicarbonate, (b) from about 15% to about 40% fatty vehicle, and (c) from about 5% to about 40% thickener in an amount to provide a paste consistency.

In accordance with the method of treatment of the present invention, the composition is applied to the tongue of the acidotic ruminant in a dosage so as to ameliorate symptoms of acidosis. Applied composition is gradually and substantially released from the tongue of the treated animal to the rumen over a period of, for example, from about two to about 10 minutes, preferably over a period of from about three to about five minutes and source of alkalinity in composition reaching the rumen is gradually released in the rumen to react with excess lactic acid therein over a period of, for example, from about 10 minutes to about six hours, preferably over a period of from about 15 minutes to about three hours.

Besides being advantageous in affording controlled release to combat excess lactic acid without the occurrence of bloat the composition herein is shelf stable as the fatty vehicle functions to protect the alkaline ingredient from decomposition during storage. The composition and method herein are additionally advantageous in respectively allowing and providing a convenient way of administering treatment.

DETAILED DESCRIPTION

The composition of the present invention preferably consists essentially by weight of (a) from about 45% to about 55% of a source of alkalinity selected from the group consisting of non-toxic carbonate, bicarbonate and sesquicarbonate, (b) from about 20% to about 30% fatty vehicle, and (c) from about 10% to about 35% thickener.

Turning now to the compounds used as the source of alkalinity, these are preferably metal salts wherein the metal is selected from the group consisting of sodium, potassuum, calcium and magnesium. Preferred compounds include sodium bicarbonate, potassium bicarbonate, sodium sesquicarbonate, alkali metal carbonates (sodium carbonate or potassium carbonate) and alkaline earth metal carbonates (calcium carbonate or magnesium carbonate). The most preferred compound is sodium bicarbonate. If desired, mixtures of compounds can be used as the source of alkalinity.

Turning now to the fatty vehicle ingredient, it preferably is derived from naturally occurring glyceride oils, such as vegetable or marine oils, or from animal fats. The term "derived from" means that the oil or other fatty ingredient is directly used as the fatty vehicle ingredient or undergoes processing to provide such ingredient. Preferably, the fatty ingredient is derived from a vegetable oil such as coconut oil, corn oil, cottonseed oil, olive oil, palm oil, peanut oil, rapeseed oil, safflower oil, sesame seed oil, soybean oil, sunflower seed oil and wallflower seed oil. Suitable marine oils include herring oil, menhaden oil, pilchard oil, salmon oil, sardine oil and whale oil. Suitable animal fat derived fatty vehicles are described in Rule 6, Section 3 of the Trading and Arbitration Rules of the American Fats & Oils Association, Inc. and include grease grades of Choice White (minimum titre, i.e. m.t., of 37, maximum free fatty acid, i.e. m.f.f.a. of 4.0 and maximum iodine units, i.e. m.i.u., of 1), "A" White (m.t. of 37, m.f.f.a. of 8.0 and m.i.u. of 1) and "B" White (m.t. of 37, m.f.f.a. of 10.0 and m.i.u. of 1) and tallow grades of Top White (m.t. of 41, m.f.f.a. of 2, m.i.u. of 1), Extra Fancy (m.t. of 41, m.f.f.a. of 3 and m.i.u. of 1) and Fancy and Bleachable Fancy (m.t. of 40.5, m.f.f.a. of 4 and m.i.u. of 1). A very desirable fatty vehicle is refined soybean oil.

As indicated above, the fatty vehicle has a double synergistic effect. Firstly, it controls release of alkaline ingredient in the rumen. Secondly, it protects against decomposition during product storage and therefore is instrumental in providing product with excellent shelf life. The release rate of alkaline ingredient in the rumen is related to the fatty vehicle to alkaline ingredient weight ratio. A weight ratio of 0.4–0.6 parts fatty vehicle to 1 part alkaline ingredient normally provides controlled release in the rumen over a period ranging from about 15 minutes to about 3 hours at the dosage rates specified hereinafter. Decreasing the ratio decreases the release period, and increasing the ratio increases the release period.

Turning now to the thickener ingredient, it preferably is selected from any of the approved food grade thickeners. Suitable thickeners include, for example, natural gums, such as gum karaya, gum arabic, gum tragacanth, guar gum, and locust bean gum; gel-forming materials such as aluminum monostearate, colloidal magnesium-aluminum silicate, finely divided silica, and clays, such as kaolin, bentonite, montmorillonite and attapulgite clays; water-soluble salts of cellulose ethers such as sodium carboxymethylcellulose, hydroxyethylcellulose and sodium carboxymethylhydroxyethylcellulose: and synthetic thickeners such as alkyl poly(oxyalkylene) esters of acrylate oligomers and copolymers thereof. Other suitable thickeners include microcrystalline cellulose, starch, and Thixcin.

The thickener is selected and used in an amount so that the composition has a paste consistency, i.e. a soft plastic consistency and preferably a consistency similar to that of peanut butter. A suitable test for determining relative consistencies is the penetration test done with the aid of a grease pentrometer according to A.S.T.M. Method D 217-52T. Penetration values are obtained by placing a standard grease cone on the surface of a sample to be penetrated and measuring the number of tenths of a millimeter the cone penetrates the sample in 5 seconds. The composition is tested for consistency as determined by penetration after the temperature of the sample is brought to 70° F. when it has been stored at higher or lower temperatures. For purposes of this invention a Precision Scientific A.S.T.M. Pentrometer with a 47 g. cone on a 9" shaft, the cone measuring 2"×19/32", is used. Using this instrument the desired range of penetration values is normally from about 175 to about 300 mm./10. A penetration value less than 175 normally indicates too firm a product, while a penetration value of more than about 300 normally will indicate a product which is susceptible to oil separation.

In a preferred composition, the thickener comprises kaolin present in an amount ranging from about 10% to about 30% by weight of the composition used in combination with aluminum monostearate present in an amount ranging from about 0.5% to about 4% by weight of the composition.

As indicated above, the selected consistency is very important in that it causes the composition to stick to the animal's tongue when applied thereto so that the composition is controllably released from the tongue to the rumen and so that the animal after dosing has a tendency to roll its tongue with a motion allowing for expelling of formed gas, whereby the possibility of bloat occurring is minimized.

Turning now to the method of preparing the composition herein, the order and manner of admixing the ingredients is not critical. In respect to a preferred composition consisting of sodium bicarbonate, refined soybean oil, kaolin and aluminum monostearate, product is preferably prepared as follows: the aluminum monostearate is dispersed in the oil, and the admixture is heated to 120°–140° C., with stirring. The admixture is then cooled with stirring to form a gel and the sodium bicarbonate is dispersed therein. Then the kaolin is slowly incorporated.

Turning now to the dosage, the composition is normally administered to provide the dose of from about 0.1 to about 0.5 grams of sodium bicarbonate or alkalinity equivalent thereof per pound of animal per day. It is normally advantageous to administer the composition in one application per day for two to three days.

The composition is preferably administered by applying the same to the top back portion of the animal's tongue. The composition is preferably packaged in a tube or cartridge and is applied using a conventional caulking gun by inserting the gun into the animal's mouth and injecting the composition from the tube or cartridge onto the animal's tongue. Different size animals are readily accommodated by providing a plurality of cartridge sizes.

The composition herein is capable of being used as a treatment for acidosis rather than a preventative such as feed containing sodium bicarbonate and/or sodium bentonite and thus does not need to be administered on a continuing basis with the attendant risk of urinary calculi. The composition and application method herein provide controlled release of alkaline agent and thus minimize risk of bloat. the composition is shelf stable and resists decomposition. The composition permits the convenient application method of the invention. The composition and application method herein ameliorate the symptoms of acidosis and save a significant percentage of animals who might otherwise die. In addition treated animals may show a gain in weight rather than a loss normally encountered in acidotic animals.

The invention is illustrated in the following detailed example.

EXAMPLE

Acidosis treatment composition is made up according to the following composition:

| Ingredient | Parts By Weight |
|---|---|
| Sodium Bicarbonate USP | 500 |
| Kaolin USP | 230 |
| Aluminum Monostearate USP | 14.85 |
| Soybean Oil, Refined (IV = 120 to 140) | 255.15 |

The composition is prepared as follows: The aluminum monostearate is dispersed in the oil and the admixture is heated to 130° C., with stirring. The admixture is then cooled with stirring to form a gel, and the sodium bicarbonate is dispersed in the gel. Then, the kaolin is slowly incorporated. The finished product has a consistency of peanut butter. The finished product is packaged in tubes with each tube holding 320 grams of treatment composition (160 grams of sodium bicarbonate).

Composition having the formula set forth above was tested in the treatment of acidotic steers against a control group and against treatment using aqueous sodium bicarbonate solution. The treatment composition is administered by injecting from a tube using a caulking gun onto the back top portion of the treated animal's tongue. The aqueous sodium bicarbonate solution is administered by pumping treatment solution into the treated animal's rumen. The treatment using the composition of the invention is referred to hereinafter as paste treatment. The treatment using aqueous sodium bicarbonate solution is referred to hereinafter as aqueous bicarbonate or aqueous sodium bicarbonate treatment or treatment with sodium bicarbonate and water. The control group received no treatment.

The comparison study was carried out as follows.

Twenty head of Holstein steers were received on day 1. The average incoming weight for an animal was 560 lbs. The cattle were eartaged and weighed upon receipt. The steers were then placed on irrigated grass pasture to determine baseline physiological values.

Indwelling arterial catheters were placed in the tail by a veterinarian on days 2 and 3. All of the surgery was done under a local anesthetic and the animals remained standing throughout. Antibiotic was given at the time of surgery. The tails were wrapped with the catheters completely covered. This was done to provide the most protection for the catheters. Wraps were replaced and cleaned as needed throughout the trial.

The cattle were weighed on the morning of day 4 and daily thereafter through day 14.

All of the cattle were bled on days 4, 6 and 8. The resulting samples were analysed for pH, $pCO_2$, $pO_2$, base excess, bicarbonate, total $CO_2$, hemoglobin, hematocrit and plasma protein. The serum was then pooled by animal for the determination of sodium, potassium and chloride. This provided a baseline value for each individual animal.

At 5 p.m. on day 8 the cattle were assigned to treatment groups as follows: 8 head-paste treatment; 8 head-control; 4 head-aqueous sodium bicarbonate.

The cattle were placed in pens with 4 head/pen. Feed was withheld from all of the cattle from 5 p.m. on day 8 to 5 p.m. on day 9. The cattle had access to water at all times throughout the trial. During this 24 hour period, a weather front passed through the area. The weather throughout the trial was hot, mid 90's, during the day and in the upper 60's during the early morning hours.

The cattle were weighed on the morning of day 9. A 90% concentrate ration was fed free choice at 5 p.m. on day 9. The cattle consumed 35 lbs./head in the following 20 hours. The ration fed was balanced to meet industry standards.

The analysis of the gram mix constituting the ration is set forth below:

| | As Received | 100% Dry Basis |
|---|---|---|
| Laboratory Values | | |
| Dry Matter | 92.34 | % |
| Moisture | 7.66 | % |
| Crude Protein | 10.75 | 11.64% |
| Acid Detergent Fiber | 9.69 | 10.49% |
| Total Ash | 3.54 | 3.83% |
| Potassium | 0.69 | 0.75% |
| Sodium | 0.18 | 0.19% |
| Calcium | 0.51 | 0.55% |
| Magnesium | 0.15 | 0.16% |
| Phosphorus | 0.31 | 0.34% |
| Chlorine | 0.07 | 0.08% |
| Sulfur | 0.02 | 0.02% |
| Estimated Values | | |
| Digestible Protein | 6.99 | 7.57% |
| Total Digestible Nutrients | 71.39 | 77.32% |
| Metabolizable Energy | 1,258 | 1,362 KCAL/LB |
| Net Energy for Maintenance | 835 | 904 KCAL/LB |
| Net Energy for Gain | 547 | 592 KCAL/LB |
| Net Energy for Milk | 812 | 880 KCAL/LB |

By 10 p.m. on day 9, approximately 20% of the cattle showed observable symptoms of acidosis. The cattle showed scours, hard breathing, some dehydration and a few had slobbers. None of the cattle were showing any interest in feed by this time. One animal was down in the pen and would not get up.

At 1 p.m. on day 10, 45–50% of the cattle were showing observable symptoms of moderate to severe acidosis. These symptoms included scours, slobbers, lack of coordination and visible evidence of dehydration. At this time, 4 head were down in the pens and would not get up. The decision was made to begin treatment of the cattle. The paste group was given ½ of a tube of paste, (equivalent to approximately 80 gms. of sodium bicarbonate) and the aqueous bicarbonate group was given 200 gms. of sodium bicarbonate in 2 L of warm water, administered by stomach tube. Control cattle received no treatment.

The paste and the aqueous bicarbonate treated cattle were bled approximately 1 hour after the first treatment. Response to paste treatment appeared to be very slow and the decision was made to give another ½ tube per animal. After this treatment, the paste treated animals visibly looked better than the control cattle. There was no visible difference between the paste and aqueous bicarbonate treated cattle.

The cattle were all bled late on the evening of day 10. One of the control cattle was very sick and unable to stand at 11 p.m. By midnight he had died. The remaining cattle were all still visibly acidotic and showed no interest in food.

By the morning of day 11, the paste and aqueous bicarbonate treated cattle were still showing observable signs of acidosis. These cattle were again treated, the paste cattle with 1 tube of acidosis paste and the aqueous bicarbonate cattle with 200 gms. sodium bicarbonate in 2 L of warm water. The paste treated cattle showed improvement within one hour of treatment. Two of the four cattle in the aqueous bicarbonate treated group showed signs of bloat almost immediately after the administration of the treatment. Both of these cattle were in states of uncompensated metabolic alkalosis following treatment. A third steer in the aqueous bicarbonate treated group showed signs of respiratory alkalosis.

The control group was extremely acidotic on the morning of day 11. All of the cattle in this group showed observable symptoms of acidosis. These signs included severe scours, slobbers, visual dehydration, and loss of muscle coordination. The blood gas measurements on these cattle indicated either a metabolic acidosis or a true organic acidosis. Symptomology of acidosis was apparent in all of the cattle. There were 3 of the 7 head that could not stand. All of the control cattle were scoured and dehydrated.

One hour after treatment the paste treated cattle were visibly improving. The metabolic state of this group ranged from normal acid/base balance to uncompensated metabolic acidosis with respiratory alkalosis. There was a definite trend in all of the paste cattle toward compensation of the acidosis.

Grass hay was fed free choice at 11 a.m. on day 11. All of the standing cattle went to feed for at least a short period of time. Throughout the day, the cattle had access to grass hay. By the end of day 11, all of the paste treated and aqueous sodium bicarbonate treated cattle were standing and eating. The control cattle were still visibly sicker and two head were not able to stand.

Blood samples were drawn on an "as needed" basis between days 10 and 12. Whenever possible, the animal was in the chute and weights were also obtained.

On the morning of day 12, all of the cattle were visibly improving. Only one calf in the control group still could not stand. There were still signs of acidosis, i.e. scouring, labored breathing, and slobbers, present in approximately 40% of all the cattle. The decision was made to treat the paste cattle with ½ tube of paste. Several of the cattle also had respiratory problems. These were characterized by snotty noses, labored breathing and a slight elevation in temperature. Any cattle showing these symptoms were treated with Liquamycin-LA.

By the afternoon of day 13, the cattle were all recovered enough to go out to the corral. The cattle were maintained on a ration of grass hay until day 15. Blood samples were drawn in the afternoon of days 13 and 14, and on the morning of day 15. By day 15 there was no significant difference in the bicarbonate levels between the control, aqueous bicarbonate and paste treated cattle. The bicarbonate levels in all of the treatment groups were all within 24 meq/L +/−0.5 meq/L. At this point, the catheters were removed and the cattle were returned to grass pasture.

All of the blood samples after the baseline period were analysed for plasma sodium, potassium and chloride. The anion gap (Na-Cl-HCO3) was calculated as well as the metabolic state of the animal.

This trial simulated a severe "feed wreck" where cattle were received into a feedlot on the wrong ration. Instead of the low energy ration usually fed to new cattle, these cattle were fed a typical high energy, finish ration. This mistake nearly always results in a group of feedsick, acidotic, cattle. In this trial, a state of severe acidosis was induced in all of the cattle on trial. The severity of the acidosis, prior to treatment, was uniform across all of the pens of cattle. Approximately one half of the cattle were identified as having a true organic acidosis.

The cattle treated with the paste did not become as acidotic as the control cattle. The bicarbonate and the base excess, both measures of available buffering capacity, were significantly higher in the paste treated cattle. Although the paste treated cattle still showed some observable symptoms of acidosis, the severity was much less than in the control cattle. Some of the paste treated cattle showed a slight metabolic alkalosis after treatment. This metabolic state was not severe and did not last very long. The recovery of these cattle was visually and metabolically faster and better than the untreated control cattle.

The cattle treated with sodium bicarbonate and water were also visibly better than the control cattle. This treatment group did, however, show some negative side effects. Two of the four cattle in this group showed signs of moderate to severe bloat immediately after drenching with the sodium bicarbonate and water. Although neither of these animals were treated for bloat, this danger is significant. Metabolically these cattle were alkalotic and often uncompensated. Three of the four cattle in this group showed signs of uncompensated metabolic or respiratory acidosis. The visible recovery of these cattle from the acidosis was comparable to the cattle treated with paste. The metabolic recovery however, was not. Where the paste treated cattle returned to normal acid/base balance more slowly, no signs of prolonged metabolic alkalosis were seen. Three of the four bicarbonate and water cattle showed signs of prolonged metabolic alkalosis.

The control cattle were visibly and metabolically acidotic. The observable symptoms were scours, slobbering, labored breathing and lack of muscle coordination. These cattle showed negative base excess values and very low bicarbonate values while visibly acidotic. The recovery was low. One steer died on the first day after return of full feed, day 10. This steer was unable to stand for at least 16 hours prior to death. One other steer was also unable to stand for 12 hours between days 10 and 11. While he could not stand, water and hay were hauled to him. This steer probably would not have survived in a typical feedlot situation.

The weight changes that occured during this trial should be noted. As can be seen from the following table which recites daily mean weights, the paste treated cattle actually finished the trial gaining weight. The bicarbonate and water treated cattle lost weight. This shows that the effects of alkalosis on performance can be as detrimental as the effects of acidosis. The control cattle, as expected, lost the most weight during the course of the trial.

TABLE

| Day | Control* | Paste | Aqueous Bicarbonate |
|---|---|---|---|
| 4 | 572.6 lbs. | 558.1 lbs. | 557.0 lbs. |

TABLE-continued

| Day | Control* | Paste | Aqueous Bicarbonate |
|---|---|---|---|
| 5 | 566.4 | 558.8 | 552.5 |
| 6 | 569.3 | 565.0 | 560.0 |
| 7 | 563.3 | 555.4 | 556.8 |
| 8 | 575.7 | 569.5 | 574.5 |
| 9 | 552.6 | 540.3 | 568.5 |
| 10 | 575.6 | 568.8 | 566.3 |
| 11 | 560.1 | 550.4 | 549.0 |
| 12 | 549.4 | 552.9 | 553.5 |
| 13 | 554.7 | 564.0 | 555.0 |
| 14 | 554.7 | 567.1 | 555.8 |

*This data includes 7 head; it excludes the animal that died.

The data from this trial indicates that the acidosis paste is beneficial in the treatment of acidosis in cattle. The paste treatment reduces the severity of the acidosis and enhances the subsequent recovery. No signs of prolonged metabolic alkalosis were observed in these cattle. The ease of treatment with the paste was also an advantage. From the data and the visible animal response, it can be inferred that the release of the bicarbonate in the oil based paste is slower and more controled than the release of aqueous sodium bicarbonate.

The bicarbonate and water group did recover from the acidosis as rapidly as the paste treated cattle; however, the side effects of bloat, prolonged metabolic alkalosis and subsequent poor performance limit the use of this treatment. From a practical basis, the use of a stomach pump and drench tube is also not feasible on a large scale.

Results similar to those obtained above of ameliorating the symptoms of acidosis without bloat are obtained when equivalent amounts of sodium sesquicarbonate or potassium bicarbonate or sodium carbonate or potassium carbonate or calcium carbonate or magnesium carbonate are substituted in the above formulation in place of part or all of the sodium bicarbonate.

Other variations will be evident to those skilled in the art. Therefore, the scope of the invention is intended to be defined by the claims.

What is claimed is:

1. Method of treating ruminants for acidosis comprising applying to the tongue of the ruminant for gradual swallowing a composition in a dosage to provide from about 0.1 to about 0.5 grams of sodium bicarbonate or alkalinity equivalent thereof per lb. of animal per day so as to ameliorate symptoms of acidosis, said composition consisting essentially by weight of
    (a) from about 40% to about 60% of a source of alkalinity selected from the group consisting of non-toxic carbonate, bicarbonate and sesquicarbonate,
    (b) from about 15% to about 40% fatty vehicle, and
    (c) from about 5% to about 40% thickener in an amount to obtain a paste consistency.

2. Method asa recited in claim 1, wherein the composition applied to the tongue is gradually released from the tongue to the rumen over a period of from about two to about 10 minutes.

3. Method as recited in claim 2, wherein the composition applied to the tongue is gradually released from the tongue to the rumen over a period of from about three to about five minutes.

4. Method as recited in claim 3, wherein the source of alkalinity in said composition reaching the rumen is gradually released in the rumen to react with lactic acid therein over a period ranging from about 10 minutes to about 6 hours.

5. Method as recited in claim 4, wherein the composition is applied by injecting it from a tube onto the top back portion of the animal's tongue.

6. Method as recited in claim 5, wherein said composition consists essentially by weight of from about 45% to about 55% source of alkalinity, from about 20% to about 30% fatty vehicle and from about 10% to about 35% thickener.

7. Method as recited in claim 6, wherein the source of alkalinity in the composition is sodium bicarbonate and the fatty vehicle in the composition is derived from vegetable oil.

8. Method as recited in claim 7, wherein the composition contains as thickener from about 10% to about 30% by weight kaolin and from about 0.5% to about 4% aluminum monostearate.

9. Method as recited in claim 8, wherein the composition has a consistency characterized by a penetration value ranging from about 175 to about 300 mm/10.

* * * * *